(12) United States Patent
Patel et al.

(10) Patent No.: US 7,723,278 B2
(45) Date of Patent: May 25, 2010

(54) STABLE, SUBSTANTIALLY SURFACTANT-FREE LIQUID COMPOSITIONS COMPRISING HYDROPHOBIC PHASE

(75) Inventors: Rajesh Patel, Middlebury, CT (US); Rosa Mercedes Paredes, Shelton, CT (US)

(73) Assignee: Conopco Inc., Englewood Cliffs, NJ (US)

( * ) Notice: Subject to any disclaimer, the term of this patent is extended or adjusted under 35 U.S.C. 154(b) by 218 days.

(21) Appl. No.: 11/748,943

(22) Filed: May 15, 2007

(65) Prior Publication Data

US 2008/0287336 A1 Nov. 20, 2008

(51) Int. Cl.
*A61K 7/00* (2006.01)
(52) U.S. Cl. ............ 510/130; 510/159; 510/475; 510/488; 510/463; 510/421
(58) Field of Classification Search ............ None
See application file for complete search history.

(56) References Cited

U.S. PATENT DOCUMENTS

| 5,427,704 | A | 6/1995 | Lawate |
| 5,472,728 | A | 12/1995 | Miller et al. |
| 5,490,995 | A | 2/1996 | Corrigan |
| 5,578,299 | A | 11/1996 | Starch |
| 5,888,492 | A | 3/1999 | Starch |
| 5,928,632 | A | 7/1999 | Reusch |
| 6,156,369 | A | 12/2000 | Eger et al. |
| 6,645,511 | B2 | 11/2003 | Aronson et al. |
| 6,699,488 | B2 | 3/2004 | Deckner et al. |
| 6,716,440 | B2 | 4/2004 | Aronson et al. |
| 6,780,826 | B2 | 8/2004 | Zhang et al. |
| 6,903,057 | B1 | 6/2005 | Tsaur |
| 6,998,382 | B2 | 2/2006 | Yang et al. |
| 2004/0223992 | A1 | 11/2004 | Clapp et al. |
| 2007/0032393 | A1 | 2/2007 | Patel et al. |

FOREIGN PATENT DOCUMENTS

| EP | 398 409 | 11/1990 |
| WO | WO2007017118 | * 2/2007 |

* cited by examiner

*Primary Examiner*—Necholus Ogden, Jr.
(74) *Attorney, Agent, or Firm*—Ronald A. Koatz

(57) ABSTRACT

The present invention relates to substantially surfactant-free liquid compositions comprising moderate levels of oil. By limiting amount of oil and using aqueous phase structuring agent, it is possible to provide stable and optionally translucent compositions.

2 Claims, 2 Drawing Sheets

Lotion gel

Lotion
 gel

STABLE, SUBSTANTIALLY SURFACTANT-FREE LIQUID COMPOSITIONS COMPRISING HYDROPHOBIC PHASE

FIELD OF THE INVENTION

The present invention relates to liquid compositions, preferably aqueous liquid compositions, comprising a moderate, but not excessive amount of hydrophobic phase (e.g., oil, or structured oil functioning as benefit agent). In particular, the invention relates to such compositions comprising substantially no surfactant (which typically helps stabilize hydrophobic phase), yet in which the hydrophobic phase (e.g., 1 to 14, preferably 2 to 13%, more preferably 2 to 12% of a thickened or un-thickened oil) remains stable.

BACKGROUND

Liquid compositions comprising a hydrophobic phase, e.g., oil phase are known. Typically, such compositions comprise either at least a small amount of surfactant (to help stabilize hydrophobic component), at least a certain amount of hydrophobic phase/oil (i.e., at least 15%) or both.

U.S. Pat. Nos. 6,645,511 and 6,716,440, both to Aronson et al., for example, both disclose wet skin compositions comprising an aqueous phase containing dispersion stabilizer and a structured oil phase. All examples comprise at least some amount of surfactant or, in the only example where there is not at least some surfactant emulsifier (see, for example, Example 8H at column 27-28, Table 8 of U.S. Pat. No. 6,645,511), at least 15% oil. Also, the oil phase is always structured. In at least one embodiment of the subject invention, the emollient or hydrophobic phase is not structured.

Other references disclosing liquid compositions comprising a hydrophobic phase and a surfactant include U.S. Pat. No. 6,780,826 to Zhang et al. and U.S. Pat. No. 6,998,382 to Yang et al.

U.S. Pat. No. 6,699,488 to Deckner discloses liquid compositions comprising high internal phase emulsions (e.g., hydrocarbon oils, waxes, silicones, etc. as defined). These skin containing compositions must comprise at least 20% oil.

Use of some surfactant and/or relatively higher amounts of oil was believed necessary to achieve compositions which are stable. By stable is meant that the is emulsion will not phase separate when kept in storage at 40° C. for at least two weeks, preferably at least 50° C. for three months.

Unexpectedly, applicants have found that use of structurants (e.g., cross-linked acrylate/methacrylate polymers such as Carbopol®) in the aqueous phase allows preparation of stable compositions without surfactant and using relatively modest amounts of hydrophobic phase (e.g., oil).

Absence of surfactant can be beneficial in that there is no interaction between surfactant and hydrophobic phase, thereby allowing preparation of relatively clear or transparent aqueous gels. This in turn allows ingredients to be used which may provide visual effects marketable to consumer. In addition, use of lower amounts of oil results in cost savings.

BRIEF SUMMARY OF THE INVENTION

More specifically, the invention relates to liquid compositions, preferably compositions comprising greater than 60%, more preferably greater than 65%, up to 90% water having formulation as follows:

(1) a hydrophobic phase comprising 1 to 14%, preferably 1 to 13%, more preferably 2 to 12%, more preferably 3 to 11% by wt. (by wt. of total composition) of a hydrophobic emollient (oil phase),
    wherein said hydrophobic component (e.g., emollient or oil) may or may not be thickened or structured, and wherein hydrophobic phase further optionally comprises 0 to 5% fatty acid (by wt. total composition);

(2) an aqueous phase comprising
    (a) greater than 60%, preferably greater than 65% (up to 90%) by wt. water;
    (b) 5 to 25%, preferably 7 to 20% by wt. of a hydrophilic benefit agent,
    (c) 0.1-10%, preferably 0.2 to 8% by wt. of an aqueous phase stabilizer;
    (d) Balance minors (e.g., perfumes, preservatives);
    wherein said composition has substantially no surfactant (i.e., less than 0.5%, preferably less than 0.2%, preferably none).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF INVENTION

The present invention relates to liquid compositions, commonly used in the shower and often referred to as shower gel compositions.

Such shower gel compositions typically contain low levels (although at least some) of surfactants and relatively high levels of an oil or emollient (e.g., hydrophilic benefit agent). They are often applied after cleansing, during rinse, and are used to achieve deposition of the oil or emollient. Thus, they are also known as rinse-off conditioners.

As indicated above, even though they typically have low levels of surfactants, these compositions typically will have some small amount of surfactant (acting as emulsifier for hydrophobic emollient phase) and/or relatively high levels of hydrophilic emollient. The subject invention is directed to compositions which have substantially no surfactant emulsifier, yet are able to maintain stable (no phase separation of emollient phase after 3 months at 40° C.). These compositions use aqueous phase stabilizers (e.g., any suspending polymers) rather than surfactant to provide stability. The compositions use lower amounts of hydrophobic emollient than used in other references. Specifically, applicants have found that, by using aqueous phase stabilizers rather than surfactant, the surfactant does not emulsify oil and, surprisingly, less oil can be used to provide same effect.

In addition, because the surfactant/emulsifier is absent, it is possible to make more translucent compositions rather than creamy, white, more opaque emulsions. This means that components can be incorporated into the compositions that provide greater visual benefits.

Figure 1:
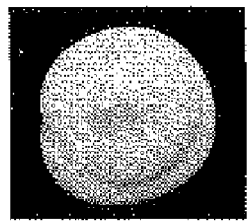
FIG. 1 shows a translucent gel of the invention versus a more opaque lotion.
Figure 1:
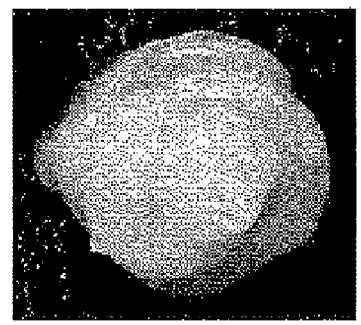
Figure 2:
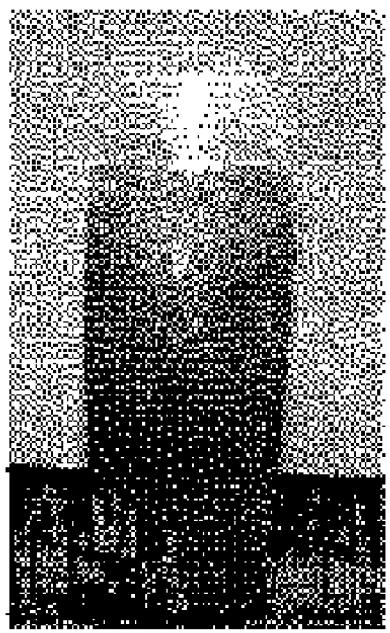
FIG. 2 shows examples of color (dyes) that can be added to the translucent gel to provide desired optical affect.
Figure 2:
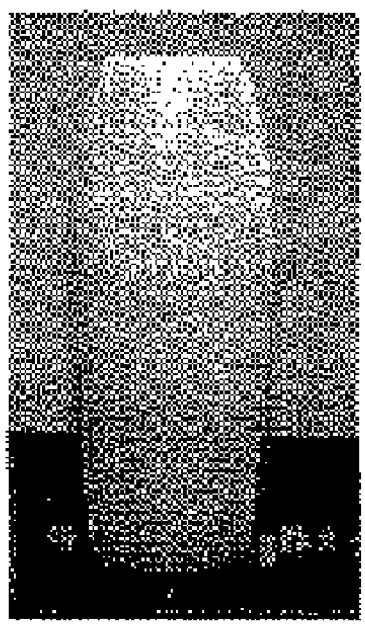

FIG. 1 shows example of more translucent gel compared to lotion with more oil. FIG. 2 shows gels with colors to achieve beautiful visual effects.

By compositions having "substantially no surfactant" is meant compositions which have less than 1%, preferably less than 0.5%, preferably less than 0.2%, more preferably less than 0.1% surfactant. In some compositions, surfactant may be absent altogether. By surfactant is meant anionic, nonionic, cationic and amphoteric surfactants as are known in the art. This also includes soap surfactants.

By "translucent" is meant that definition which is generally employed and is generally in accordance with the usual dictionary definition. For example, a translucent liquid is one that allows light to pass through it but the light may be so scattered, by for example polymers or structurants, such that it is not possible to clearly identify objects behind the translucent liquid. Translucent liquid composition may include colorless or colored liquids.

The compositions of the invention are defined in more detail below.

Hydrophobic Phase

Emollient/Oil

The hydrophobic emollients of the invention are typically skin compatible oils by which is meant oils that are liquid at temperature at which bathing is carried out, and which are safe for use in cosmetics because they are inert to the skin or actually beneficial. Examples of such skin compatible oils include ester oils, hydrocarbon oils and silicone oils.

Ester oils as the name implies have at least one ester group in the molecule. One type of common ester oil useful in the present invention are the fatty acid mono and polyesters such as cetyl octanoate, octyl isonanoanate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester, sorbitol ester, and the like.

A second type of useful esters oil is predominantly comprised of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature, Modified triglycerides include materials such as ethoxylated and maleated triglyceride derivatives, provided they are liquids. Proprietary ester blends such as those sold by Finetex as Finsolv® are also suitable, as is ethylhexanoic acid glyceride.

A third type of ester oil is liquid polyester formed from the reaction of a dicarboxylic acid and a diol. An example of polyesters suitable for the present invention is the polyesters marketed by ExxonMobil under the trade name PURESYN ESTER®.

A second class of skin compatible oils suitable for the present invention is liquid hydrocarbons. These include linear and branched oils such as liquid paraffin, squalene, squalane, mineral oil, low viscosity synthetic hydrocarbons such as polyalphaolefin sold by ExxonMobil under the trade name of PureSyn PAO® and polybutene under the trade name PANALANE® or INDOPOL®. Light (low viscosity) highly branched hydrocarbon oils are also suitable.

Petrolatum is a unique hydrocarbon material and a useful component of the present invention. Since it is only partially comprised of a liquid fraction at room temperature, it may be regarded as "structured oil phase" when present by itself or alternatively as a "structurant" when admixed with other skin compatible oils.

A third class of useful skin compatible oils is silicone based. They include linear and cyclic polydimethyl siloxane, organo functional silicones (alkyl and alkyl aryl), and amino silicones. Silicones may include pre-made emulsions such as Silicone 1788® from Dow Chemical.

In one embodiment of the invention, the emollient or oil may be structured to create a structured oil phase. As indicated above, petrolatum may itself be considered a "Structured Phase".

The structurant may, for example, be either an organic or inorganic structurant. Preferred inorganic structurants are hydrophobically modified silica or hydrophobically modified clay with particle size less than 1 micrometer. Examples are Bentone 27V, Bentone 38V or Bentone gel MIO V from Rheox, and Cab-O-Sil TS720 or Cab-O-Sil M5 from Cabot Corporation.

The organic structurants are either crystalline solids or amorphous gels with molecular weight less than 5,000 Daltons, preferably less than 3,000 Daltons.

Preferred organic structurants have a melting point greater than 35° C., preferably greater than 40° C. Especially preferred structurants are those that can form a solution with the selected skin compatible oil at a temperature higher than their melting point to form a free flowing clear solution. Upon cooling to the ambient temperature, the organic structurant precipitate from the oil phase to form a 3-dimensional crystal structure providing the physical properties set forth above.

Examples of organic thickeners suitable for the invention are solid fatty acid esters, natural or modified fats, fatty acid, fatty amine, fatty alcohol, natural and synthetic waxes, and petrolatum. Petrolatum is a preferred organic structuring agents.

Particularly preferred organic structurants are solid fatty acid esters and petrolatum. Examples of solid fatty esters are mono, di or tri glycerides derivatives of palmitic acid, stearic acid, or hydroxystearic acid; sugar fatty ester or fatty esters of dextrin. Examples of these polyol fatty acid esters are described in U.S. Pat. Nos. 5,427,704, 5,472,728, 6,156,369, 5,490,995 and EP Patent 398 409 incorporated by reference herein. Trihydroxystearin sold under the trade name of THIXCIN R from Rheox Corporation is found particularly useful for structuring triglyceride ester oils.

The level of structurant present in a structured oil phase can be in the range of 1 to 90% and depends on the type of structurant used and the nature of the skin compatible oil. For solid organic structurants such as trihydroxystearin, the preferred level is 3 to 15%. Preferably, the exact levels used should provide a stable network having the desired viscosity in the range of 100 to 5000 poise measured at a shear rate of 1 Sec-1 and can be readily optimized by one skilled in the art.

The hydrophobic emollient (e.g., oil phase), as noted above, need not be structured or thickened. This is simply one embodiment since un-thickened oils may also be used. It is surprising that un-thickened oil stays stabilized simply because of stabilizer in aqueous phase.

The emollient oil found in and/or comprising the hydrophobic phase of the invention comprises 1 to 14%, preferably 1 to 13%, more preferably 2 to 12%, more preferably 3 to 11% by wt. of the total liquid composition of the invention.

In addition the hydrophobic phase may comprise 0 to 5%, preferably 1 to 4% by wt. total composition fatty acid (e.g., saturated or unsaturated $C_{14}$-$C_{24}$ fatty acid).

Aqueous Phase

Compositions of the invention also comprise an aqueous phase as noted below.

The aqueous phase typically comprise at least 60%, preferably greater than 60%, more preferably greater than 65% by wt. water.

The aqueous phase further comprises 0% to 25%, preferably 5 to 25%, preferably 7 to 20% by wt. of a hydrophilic moisturizer or skin benefit agent. Examples of such compounds are polyols such as linear and breached chain alkyl polyhydroxyl compounds. These include, for example, propylene glycol, sorbitol and glycerin.

Also polymeric polyols are useful, such as polypropylene glycol, polyethylene glycol, butylene glycol and so forth.

The aqueous phase further must comprise 0.1 to 10%, preferably 0.2 to 2.0% by wt. of a stabilizer.

Aqueous dispersion stabilizers useful in the instant invention can be organic, inorganic or polymeric stabilizers. Specifically, the compositions comprise 0.1 to 10% by wt. of an organic, inorganic or polymeric stabilizer which should provides physical stability of the oil droplets, in the surfactant composition at 37° C., 40° C. or preferably 50° C. for at least 3 months.

Inorganic dispersion stabilizers suitable for the invention includes, but are not limited to clays, and silicas. Examples of clays include smectite clay selected from the group consisting of bentonite and hectorite and mixtures thereof. Synthetic hectorite (laponite) clay used in conjunction with an electrolyte salt capable of causing the clay to thicken (alkali and alkaline earth salts such as halides, ammonium salts and sulfates) particularly useful. Bentonite is a colloidal aluminum clay sulfate. Examples of silica include amorphous silica selected from the group consisting of fumed silica and precipitated silica and mixtures thereof.

Organic dispersion stabilizer are defined here as organic molecules that have a molecular weight generally lower than 1000 Daltons and form a network in the aqueous phase that immobilizes the dispersed oil phase. This network is comprised either of amorphous solids, crystals, or liquid crystalline phase. Suitable organic dispersion stabilizers for the instant invention are well know in the art and include, but are not limited to any of several types of long chain acyl derivatives or mixtures thereof. Included are the glycol mono- di- and triesters having about 14 to about 22 carbon atoms. Preferred glycol esters include the ethylene glycol mono- and distearates, glyceryl stearates, palm oil glyceride, tripalmitin, tristearin and mixtures thereof.

Another example of organic dispersion stabilizer are alkanolamides having from about 14 to about 22 carton atoms. Preferred alkanolamides are stearic monoethanolamide, stearic diethanolamide stearic monoisopropanolamide, stearic monoethanolamide stearate and mixtures thereof.

Still another class of useful dispersion stabilizer is long chain fatty acid esters such is as stearyl stearate, stearyl palmitate, palmityl palmitate, trihydroxystearylglycerol and tristearylglycerol.

Another type of organic dispersion stabilizers is the so-called emulsifying waxes such as mixtures of cetostearyl alcohol with polysorbate 60, cetomacriogol 1000, cetrimide; a mixture of glycerol monostearate with a stearic soap, and partially neutralized stearic acid (to form a stearate gel).

Still another example of a suitable dispersion stabilizing agent is long chain amine oxides having from about 14 to about 22 atoms. Preferred amine oxides are hexadecyldimethylamine oxide and octadecyldimethylamide oxide.

Example of a suitable polymeric dispersion stabilizing agents useful in the present invention include: carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum.

An especially preferred types of polymeric dispersion stabilizer agent include acrylate containing homo and copolymers. Examples include the crosslinked poly acrylates sold by B.F. Goodrich under the CARBOPOL trade name; the hydrophobically modified cross linked polyacrylates sold by B.F. Goodrich under the PEMULEN trade name; and the alkali swellable acrylic latex polymers sold by Rohm and Haas under the ARYSOL or ACULYN trade names.

The above dispersion stabilizers can be used alone or in mixtures and may be present in an amount from about 0.1 wt. % to about 10 wt. % of the composition.

The compositions also comprise other ingredients typically founding liquid formulations.

Among these are included (without limitation) auxiliary thickeners (e.g., carboxymethyl cellulose, hydroxyethylcellulose); perfumes, sequestering agents (e.g., ethyl diamine tetra acetate, known as EDTA); cooling agents; opacifiers and pearlizers (e.g., zinc or magnesium stearate, titanium dioxide).

Other optionals include antimicrobial agents; preservatives (e.g., parabens, sorbic acid); suds boosters (e.g., coconut acyl mono- or diethanolamide); antioxidants; cationic conditioners (e.g., Merquat® and Jaguar® type conditioners); exfoliates; ionizing salts; organic acids (e.g., citric or lactic acid).

One strong advantage of using the stabilizer, relatively low oil systems of the invention is that the composition can be stabilized while creating a translucent or transparent aqueous agent rather than creamy emulsion (see FIG. 1). In such compositions, it is possible to use ingredients which create a visual cue (e.g., colored speckles) which can offer a marketing advantage (see FIG. 2).

Protocol

Stability is measured by placing product on shelf at 37° C. or 40° C., preferably at 50° C. for at least 3 months to observe whether the oil phase visually separates from the emulsion.

Opacity measurements may be taken on a Hunter Lab Color Quest 11 calorimeter capable of measuring the reflectance of light through the gel composition, first against a white background and then against a black background. Opacity can be calculated according to the equation:

$$\% \text{ Opacity} = \left[\frac{Y_{\text{black\_background}}}{Y_{\text{white\_background}}}\right] \times 100$$

Where $Y_{black\ background}$ is the reflectance value of the composition against a black background and $Y_{white\ background}$ is the reflectance value of the composition against a white background.

As reflectance increases (i.e., as translucency improves) $Y_{white\ background}$ increases and $Y_{black\ background}$ decreases. Thus, as opacity decreases, translucency increases.

EXAMPLES

Example 1

A typical example of the invention is disclosed below:

| | % by Wt. |
|---|---|
| Hydrophobic Phase* | |
| Fatty Acid | 0-5% |
| Soybean | 0-14% |
| Petrolatum | 0-15% |
| Hydrophobic Structuring agent (e.g., trihydroxy stearin) | 0-2% |
| Water Phase | |
| Ethanol (to help translucency, if desired) | 0-8% |
| Glycerol | 1-25% |
| Aqueous structuring agent (e.g., carbopol) | 0.2-2% |
| Water, fragrance, preservatives | Balance |

*oil must comprise 1-14% of total composition.

The example was prepared as follows
1) Aqueous phase structuring polymer was dispersed in aqueous phase (some polymers may need to be dispersed and neutralized). The pH range was 5.5-7.0. Heat was applied to the structuring polymer (heat may or may not be applied depending on polymer used).
2) oil phase ingredients were mixed and heated to 50° C. with temperature adjusted as needed.
3) oil phase was added to aqueous phase, mixed and homogenized as needed for oil droplet formation.

As seen, the example has substantially no surfactant and 14% or less oil, yet remains stable (i.e., composition remained phase stable at 37°, 45° and 50° C. over at least three months).

The invention claimed is:

1. A liquid composition comprising:
(1) 1 to 14% by wt. of a hydrophobic phase consisting of oil selected from the group consisting of ester oils, hydrocarbons and silicones,
wherein said hydrophobic component is not structured;
(2) an aqueous phase comprising:
(a) greater than 60% by wt. water;
(b) 5 to 25% of a hydrophilic benefit agent which is selected from the group consisting of linear or branched chain alkyl polyhydroxyl compound, polymeric polyol and mixtures thereof;
(c) 0.1-10% of an aqueous phase stabilizer which is an acrylate containing homo or copolymer;
(d) balance minors;
wherein said composition has substantially no surfactant and wherein said composition is translucent.

2. A composition according to claim 1 comprising 1 to 13% by wt. hydrophobic phase.

* * * * *